(12) United States Patent
Nakada

(10) Patent No.: US 7,024,001 B1
(45) Date of Patent: Apr. 4, 2006

(54) STETHOSCOPE

(75) Inventor: Tsutomu Nakada, Tokyo (JP)

(73) Assignee: Japan Science and Technology Corporation, Kawaguchi (JP)

( * ) Notice: Subject to any disclaimer, the term of this patent is extended or adjusted under 35 U.S.C. 154(b) by 678 days.

(21) Appl. No.: 10/089,149

(22) PCT Filed: Aug. 8, 2000

(86) PCT No.: PCT/JP00/05295

§ 371 (c)(1),
(2), (4) Date: Mar. 27, 2002

(87) PCT Pub. No.: WO01/24701

PCT Pub. Date: Apr. 12, 2001

(30) Foreign Application Priority Data

Sep. 30, 1999 (JP) .................................. 11-278605

(51) Int. Cl.
*A61B 7/04* (2006.01)
(52) U.S. Cl. .................. 381/67; 600/323; 600/473
(58) Field of Classification Search ................. 381/67; 600/544, 545, 454, 468, 310, 320, 333, 340, 600/342, 504
See application file for complete search history.

(56) References Cited

U.S. PATENT DOCUMENTS

| | | | |
|---|---|---|---|
| 4,653,498 A | 3/1987 | New, Jr. et al. | |
| 5,902,235 A | 5/1999 | Lewis et al. | |
| 6,128,517 A * | 10/2000 | Maki et al. | 600/310 |
| 6,285,896 B1 * | 9/2001 | Tobler et al. | 600/338 |
| 6,708,048 B1 * | 3/2004 | Chance | 600/322 |
| 2002/0091335 A1 * | 7/2002 | John et al. | 600/544 |

FOREIGN PATENT DOCUMENTS

JP 11-169361 6/1999

* cited by examiner

Primary Examiner—Brian T. Pendleton
(74) Attorney, Agent, or Firm—Oblon, Spivak, McClelland, Maier & Neustadt, P.C.

(57) ABSTRACT

A simple always-portable stethoscope for enabling accurate diagnosis. A radiation/light-receiving fiber (11) serving as a probe part for noninvasively irradiating a diseased part with near-infrared light is applied to the diseased part so as to measure, e.g., a change of the cerebral circulation blood flow. The change is hard as sound pulse modulation to examine the change of the cerebral function. For example, a light beam of three wavelengths $\lambda=760$, 800, 830 nm from a semiconductor laser light source (22) is applied to the diseased part, the reflection data from the diseased part is processed by a control device (21), and the doctor can make a diagnosis with the doctor's ears by hearing with a receiver (32) the change as the change of the frequency of the sound the pitch and volume of which are constant.

5 Claims, 2 Drawing Sheets

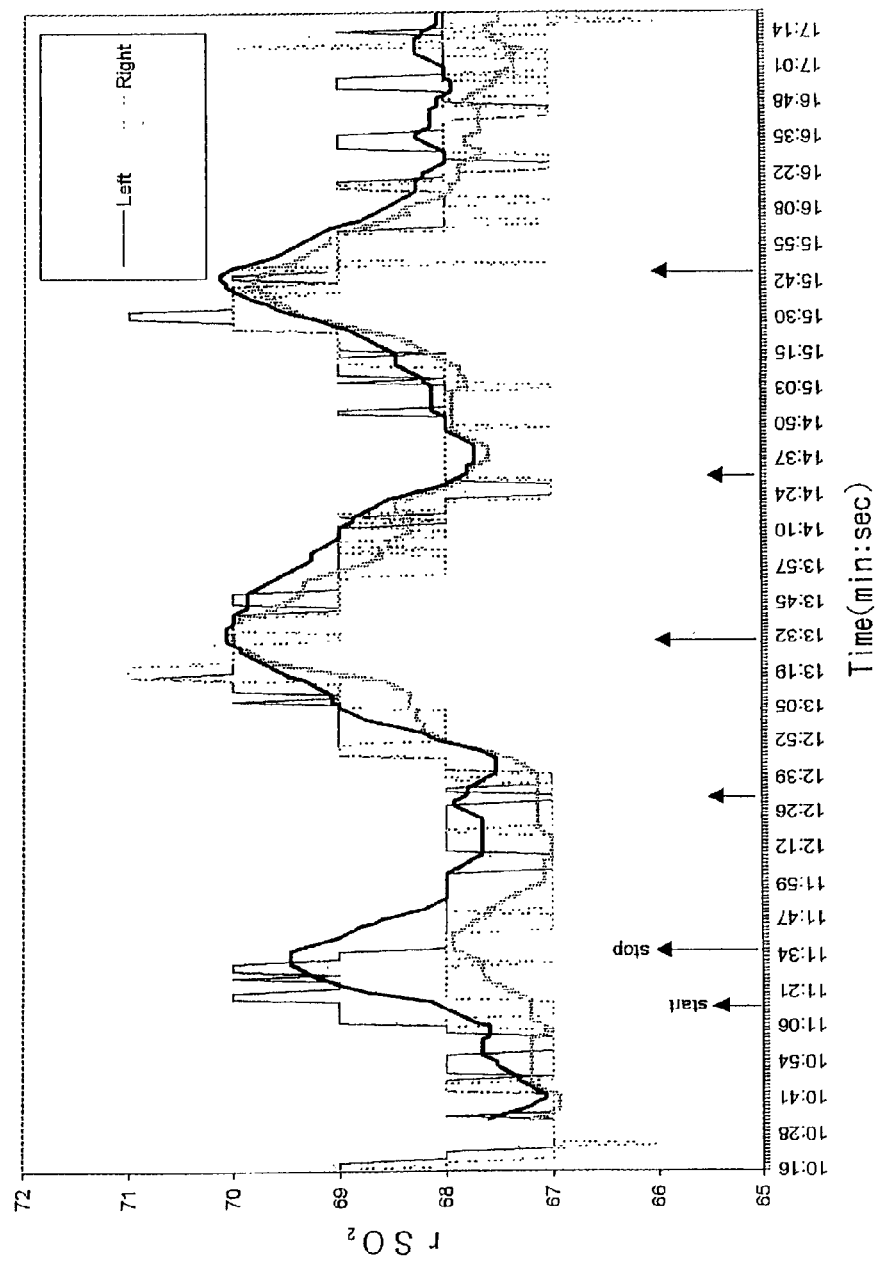

STETHOSCOPE

TECHNICAL FIELD

The present invention relates to a stethoscope, which is an instrument used by doctors in medical settings.

BACKGROUND ART

Techniques for acquiring data regarding hemoglobin of an organism by use of near-infrared light have been well known (in general, such techniques are collectively called "near-infrared spectroscopy (NIRS)").

One example application thereof is an oxymeter, which has been widely used. In recent years, functional imaging for noninvasively detecting cerebral function through detection of a change in the cerebral circulation blood flow has been widely noticed. This technique has been widely used in, for example, positron emission tomography (PET), which utilizes water labeled with $O^{15}$, and in a magnetic resonance imaging (BOLD-fMRI) which utilizes the magnetic susceptibility effect of deoxy hemoglobin. Development of a functional imaging technique (called optical CT) which utilizes near-infrared light has been pursued, because such functional imaging enables obtainment of hemoglobin information by use of near-infrared light. However, this functional imaging technique cannot be said to have been established.

Diagnostic apparatuses and tools can be divided into the following three categories.

(1) A large apparatus such as those used in connection with the above-mentioned PET and MRI, which requires a patient to go to a place where the apparatus is installed in order to receive an examination.

(2) A small apparatus, such as an electrocardiograph, an electroencephalograph, or an oxymeter, which is disposed at a bedside or in an ambulance, or a portable apparatus which is transported to the location of a patient.

(3) An instrument, such as a stethoscope, which a medical worker always carries on his person.

DISCLOSURE OF THE INVENTION

To date, the stethoscope is the only useful instrument which is categorized in the above-mentioned category (3). Meanwhile, in the above-mentioned category (2), apparatuses, such as an oxymeter, which utilize the above-described near-infrared light have been established. The concept of optical CT belongs to the above-mentioned category (1) or (2).

In view of the forgoing, an object of the present invention is to provide a simple, always-portable stethoscope for enabling accurate diagnosis.

In order to achieve the above object, the present invention provides the following:

[1] A stethoscope which comprises a probe section for noninvasively irradiating a diseased part with near-infrared light, the probe having radiation and light-receiving fibers; a control device connected to the probe section via a lead wire, the control device including a semiconductor laser light source connected to the radiation fiber, an optical detector connected to the light-receiving fiber, a controller for detecting a change in cerebral circulation blood flow on the basis of data output from the probe section, and a sound source device for converting the change in cerebral circulation blood flow to sound pulses; and a pair of lead wires and receivers connected to the sound source device of the control device, wherein auscultation is performed on the basis of the sound pulses from the sound source device in order to diagnose a change in cerebral function.

[2] A stethoscope according to [1] above, wherein the near-infrared light includes two wavelengths.

[3] A stethoscope according to [1] above, wherein the near-infrared light includes three wavelengths.

[4] A stethoscope according to [3] above, wherein the near-infrared light includes wavelengths of 760 nm, 800 nm, and 830 nm.

[5] A stethoscope according to [1] above, wherein the change in cerebral circulation blood flow is a change in total hemoglobin (t-Hb) or oxygen saturation rate of hemoglobin ($rSO_2$).

The present invention enables provision of a "functional stethoscope" which noninvasively radiates near-infrared light to a diseased part, and detects a change in the cerebral circulation blood flow, for example. The change is heard as sound pulse modulation to examine a change in the cerebral function. More specifically, a light beam of three wavelengths $\lambda$=760, 800, 830 nm which is generated by a semiconductor laser light source is applied to a diseased part; and a change in reflection data is converted to a change in pulse frequency of the sound of constant pitch and volume, to thereby enable a doctor to carry out auscultation.

BRIEF DESCRIPTION OF THE DRAWINGS

FIG. 4 is a graph showing examples of activation by higher-order cerebral activities.

BEST MODE FOR CARRYING OUT THE INVENTION

Figure 1:
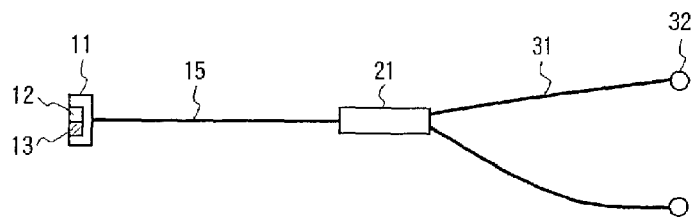
FIG. 1 is a schematic structural view of a stethoscope according to an embodiment of the present invention.

An embodiment of the present invention will next be described in detail.

A stethoscope of the present invention is adapted to detect a change in total hemoglobin (t-Hb) or oxygen saturation (regional oxygen $O_2$ saturation ($rSO_2$)) of hemoglobin and output the change in the form of sound information. The stethoscope of the present invention can be integrated with an ordinary stethoscope to thereby constitute a "smart stethoscope."

The stethoscope of the present invention is mainly used as a "functional stethoscope" which can confirm a local activation caused by cerebral function. However, the stethoscope can be used in all medical fields in which detection of a change in t-Hb or $rSO_2$ is useful. Further, application of the stethoscope of the present invention, which is a portable instrument, is expected to expand to fields which cannot be conceived presently, as has been the case with the classical stethoscope, for which doctors have found a large number of applications throughout the years, even though the classical stethoscope is an instrument which detects "sound" only.

Near-infrared spectroscopy is a technique based on the phenomenon that biological tissue exhibits optical absorbency peculiar to a constituent substance thereof. In an application for human tissue, use of light in a wavelength range of 690 nm to 880 nm, which is hardly affected by water molecules or C—H bonds, is particularly effective. Light in this region (near-infrared region) can reach a point several centimeters deep from the surface of the body. This holds true in the case of the head (brain) which is surrounded by a cranial bone. A certain substance present in a living body has a property such that its optical absorbency changes greatly with the oxygen saturation thereof, and this property enables quantification of the oxygen saturation. Representative examples of such a substance include hemoglobin, myoglobin, and cytochrom aa3. Theoretically, accurate analysis of these substances is possible. However, in principle, the present invention is directed to hemoglobin analysis without accurate quantification.

The following description of the present invention is confined to hemoglobin.

Actual optical absorbency, which is detected through sensing of reflection of radiated light, changes in accordance with the total hemoglobin t-Hb and the oxygen saturation rate of hemoglobin in a tissue under examination. Accordingly, detection of optical absorbency at a single wavelength cannot determine whether the total hemoglobin or the oxygen saturation rate changes. In view of the foregoing, optical absorbency is detected by use of at least two different wavelengths, and both the total hemoglobin and the oxygen saturation rate are estimated. In actuality, more accurate values can be calculated by use of three wavelengths. However, satisfactory results are obtained by use of two wavelengths, and in some cases use of two wavelengths is more advantageous than use of three wavelengths. Hereinafter, the embodiment will be described with reference to a calculation formula for the case in which three wavelengths are used.

One important application of the present invention is determination of "cerebral function." In the brain, cerebral functions are present in a localized manner. That is, a certain function is allocated to a certain site of the brain. At the certain site of the brain used, various metabolic changes (e.g., an increase in blood flow rate or an increase in glucose consumption) occurs. Such metabolic changes which occur at specific brain sites due to specific activities are collectively called "activation".

FIG. 4 shows an example of activation accompanying higher-order cerebral activities. This example was obtained by detecting, by means of near flared spectroscopy, changes in the oxygen saturation rate ($rSO_2$) of hemoglobin in a dorsolateral prefrontal (DLPF) portion of a patient performing a graphical test. The graph shows that a certain site of the brain is activated by the activity, and $rSO_2$ increases. During the periods between the arrows (start, stop) in FIG. 4, the patient performs the test, and the actual value of $rSO_2$ rises and falls with a slight delay.

Use of the stethoscope of the present invention enables a user to determine such activation at the patient's bedside by listening to a sound.

That is, near-infrared light of two or three wavelengths is radiated onto the brain, light reflected therefrom is sensed, and the absorbency is estimated roughly; the precise quantity of the absorbency is not obtained. The roughly estimated absorbency is converted to a sound by means of a sound source device to thereby enable diagnosis by use of the stethoscope.

Next, a specific example of the present invention will be described.

Considered here is change in the total hemoglobin, which can be obtained by an approximate expression as follows (other methods may be employed when three wavelengths are used):

$$\Delta t\text{-}Hb = 1.6 \cdot \Delta A_{780} - 5.8 \cdot \Delta A_{800} + 4.2 \cdot \Delta A_{830}.$$

Similarly, change in $rSO_2$ can be obtained by an approximate expression, as follows:

$$\Delta rSO_2 = (-3.0 \cdot \Delta A_{800} + 3.0 \Delta A_{830}) / (1.6 \cdot \Delta A_{780} - 2.8 \cdot \Delta A_{800} + 1.2 \cdot \Delta A_{830}).$$

In the expressions, each of the subscripts represents a corresponding wavelength of near-infrared light (nm). By changeover of a changeover switch, the total hemoglobin (t-Hb) or the oxygen saturation rate ($rSO_2$) of hemoglobin can be measured selectively.

Figure 2:
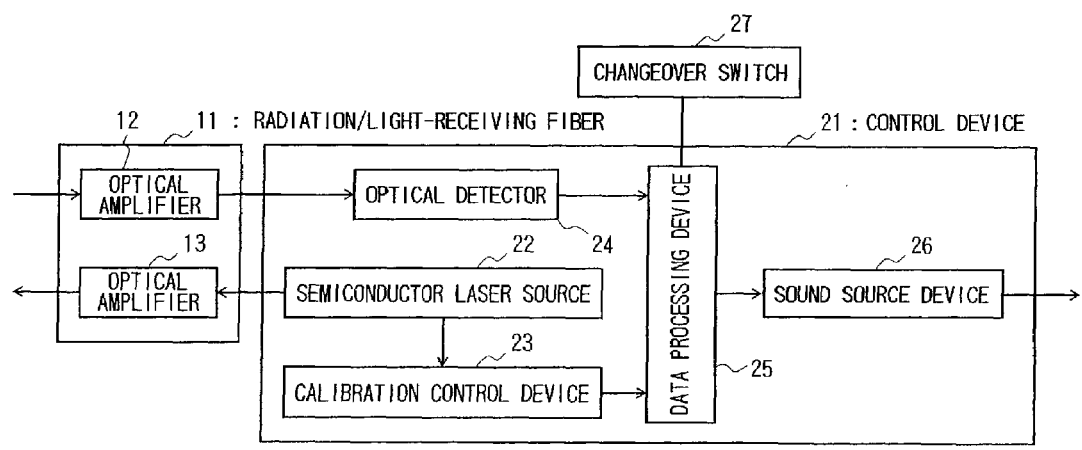
FIG. 2 is a block diagram of the stethoscope according to the embodiment of the present invention.
Figure 3:
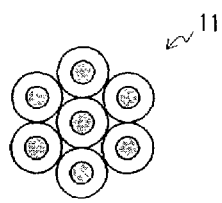
FIG. 3 is a structural view of a radiation/light-receiving fiber of a probe section of the stethoscope according to the embodiment of the present invention.

FIG. 1 is a schematic structural view of a stethoscope according to an embodiment of the present invention. FIG. 2 is a block diagram of the stethoscope. FIG. 3 is a structural view of a radiation/light-receiving fiber of a probe section of the stethoscope.

In these drawings, reference numeral 11 denotes a radiation/light-receiving fiber which serves as a probe section; 12 and 13 each denote an optical amplifier; 15 denotes a lead wire; 21 denotes a control device; 22 denotes a semiconductor laser source; 23 denotes a calibration control device; 24 denotes an optical detector; 25 denotes a data processing device (IC); 26 denotes a sound source device; and 27 denotes a changeover switch. Through use of this changeover switch 27, one of total hemoglobin (t-Hb) or the oxygen saturation rate ($rSO_2$) of hemoglobin is selected as a value to be detected. In the drawing, a power source is omitted. Reference numeral 31 denotes a lead wire connected to the sound source device 26; and 32 denotes a receiver which a doctor uses to hear sound.

As shown in FIG. 3, the radiation/light-receiving fiber which serves as a probe section of the stethoscope has a configuration such that a radiation fiber is disposed at the center, and reception fibers are disposed around the radiation fiber.

Diagnosis by use of the stethoscope is carried out as follows. That is, light of three wavelengths ($\lambda$=760, 800, 830 nm) is radiated to a diseased portion; and the control device 21 outputs a change in the reflection data. The sound source device 26 converts the change to a change in pulse frequency of a sound having a constant pitch and volume. A doctor listens to the sound from the receiver 32.

A specific operation of the sound source device 26 will now be described.

FIG. 4 shows changes in the $rSO_2$ signal in the form of a graph. In the present invention, this change (in actuality, change in the selected one of t-Hb and $rSO_2$) is indicated in the form of sound (similar to conversion between a diaphragm type and a bell type of an ordinary stethoscope).

In general, the following methods are used in order to indicate increase and decrease of a measured value by means of sound.

(1) Increase the volume of sound.

(2) Increase the pitch of sound.

However, both are difficult to sense.

In view of the foregoing, in the present invention, rise and fall of a measured value is converted to a change in the pulse frequency of a certain sound. In other words, the above conversion is similar to conversion from an "amplitude-modulated" signal to a "frequency-modulated" signal. That is, the pulse frequency of a certain sound is changed in accordance with a measured value as follows (Pi represents a sound):

Pi Pi Pi Pi

Pi Pi Pi Pi Pi Pi Pi

In this case, the latter shows that the measured value has increased.

In consideration of the psychological resolution of a medical worker, the sound source device 26 outputs not a sound used in a conventional oxymeter or the like but a sound having a constant pitch and roundness (sound corresponding to action potential in physiology). A change in t-Hb or $rSO_2$ is converted to a change in pulse frequency of sound (as in the case of neuron firing rate), and a medical worker detects the change by listening to the sound.

As described above, the stethoscope of the present invention is a useful, always-portable type instrument, which has not been introduced to doctors or other medical personnel since the invention of the classical stethoscope. The importance of the present invention is remarkable in consideration of the role which classical stethoscopes, which convey sound information only, have played in the medical field, and in view that the classical stethoscope is still the most important instrument used for diagnosis.

The present invention is not limited to the embodiments described above. Numerous modifications and variations of the present invention are possible in light of the spirit of the present invention, and they are not excluded from the scope of the present invention.

As described in detail, the present invention can provide a simple, always-portable stethoscope for enabling accurate diagnosis.

INDUSTRIAL APPLICABILITY

The present invention is suitable for the field of medical auscultatory devices, and can be applied to a functional stethoscope which enables a user to confirm a local activation caused by a cerebral function at a bedside.

What is claimed is:

1. A portable stethoscope comprising:
  (a) a probe section for noninvasively irradiating a diseased part with near-infrared light, the probe having radiation and light-receiving fibers;
  (b) a control device connected to the probe section via a lead wire, the control device including a semiconductor laser light source connected to the radiation fiber, an optical detector connected to the light-receiving fiber, a controller for detecting a change in cerebral circulation blood flow on the basis of data output from the probe section, and a sound source device for converting the change in cerebral circulation blood flow to sound pulses; and
  (c) a pair of lead wires and receivers connected to the sound source device of the control device, wherein
  (d) auscultation is performed on the basis of the sound pulses from the sound source device in order to diagnose a change in cerebral function.

2. A portable stethoscope according to claim 1, wherein the near-infrared light includes two wavelengths.

3. A portable stethoscope according to claim 1, wherein the near-infrared light includes three wavelengths.

4. A portable stethoscope according to claim 3, wherein the near-infrared light includes wavelengths of 760 nm, 800 nm, and 830 nm.

5. A portable stethoscope according to claim 1, wherein the change in cerebral circulation blood flow is a change in total hemoglobin (t-Hb) or oxygen saturation rate of hemoglobin ($rSO_2$).

* * * * *